| United States Patent [19] | [11] | 4,288,445 |
|---|---|---|
| Kusumi et al. | [45] | Sep. 8, 1981 |

[54] THERAPEUTIC COMPOSITIONS CONTAINING 4-NITROISOXAZOLE

[75] Inventors: Takenori Kusumi; Koji Nakanishi, both of New York, N.Y.

[73] Assignee: Suntory Limited, Osaka, Japan

[21] Appl. No.: 195,746

[22] Filed: Oct. 10, 1980

[51] Int. Cl.³ .............................................. A61K 31/42
[52] U.S. Cl. .................................................... 424/272
[58] Field of Search ........................................ 424/272

[56] References Cited

PUBLICATIONS

Kochetkov–Chem. Abst., vol. 54 (1960), p. 498d.

*Primary Examiner*—Sam Rosen
*Attorney, Agent, or Firm*—Wyatt, Gerber, Shoup, Scobey & Badie

[57] ABSTRACT

The compound 4-nitroisoxazole is useful as a vasodilator and smooth muscle relaxant.

10 Claims, No Drawings

THERAPEUTIC COMPOSITIONS CONTAINING 4-NITROISOXAZOLE

This invention relates to a pharmaceutically active compound useful for its properties as a vasodilator and smooth muscle relaxant, to novel pharmaceutical compositions containing the compound and to the use of the compound in the treatment of mammallian diseases requiring vasodilation or relaxation of the smooth muscles. It relates also to a novel method for preparing the compound.

The compound of this invention is the known compound 4-nitroisoxazole.

The best known synthesis of the compound is the procedure of Kochetkov et al, Zhur. Obshei Khim., 29, 535 (1959). In this procedure, the isoxazole is nitrated with a mixture of fuming nitric acid. The procedure is not however satisfactory because the yield is usually less than ten percent of theoretical.

According to the novel method of this invention, isoxazole is nitrated in a reaction inert, dry, polar organic solvent at a temperature of from 20° C. during a period of from 1 to 3 hours by reaction with at least a molar equivalent, preferably a 10% to 20% molar excess of nitronium tetrafluoroborate. The yield may be somewhat enhanced if the reaction mixture is agitated for an additional period, for example 16 to 24 hours at ambient temperature after the initial reaction period. It is not necessary to do so however.

The reaction product may be isolated in any convenient manner. Since it is insoluble in water, it is convenient to precipitate it by pouring the reaction mixture into cold water or, preferably, onto ice. The crude precipitate may be purified by extraction with a water imiscible solvent, for example ether followed by concentration and chromatographic separation. Silica gel is a convenient adsorbent.

The preferred polar organic solvent is tetrahydrophene 1,1 dioxide (sulfolane), although other solvents may also be employed. These include, for example, dimethyl formamide, dimethyl sulfoxide and straight chain and cyclic ethers such as dioxane and di-n-butyl ether.

The compound 4-nitroisoxazole is newly discovered to be useful as a smooth muscle relaxant and as a vasodilator. It relaxes the smooth muscles of the larger blood vessels especially coronary, systemic peripheral, cerebral and pulmonary arteries. It is particularly useful for the relief of cerebral and peripheral ischemia associated with arterial spasm and myocardial ischemia which may be complicated with arrythmias.

The compound has a high order of activity in coronary artery dilation when tested on guinea pig isolated heart muscle by the Langendorf profusion technique. It is also active for control of spasmolytic acitvity when tested by the Magnus technique on isolated guinea pig ileum muscle.

When the compound used in this invention is employed therapeutically, it may be administered to warm-blooded mammals in need of vasodilation type activity alone or in combination with pharmaceutically acceptable carriers, the proportion of which is determined by the solubility and chemical nature of the compound, chosen route of administration and standard pharmaceutical practice. For example, it may be administered orally in the form of tablets, capsules, lozenges, and the like which may be enteric coated and contain such excipients as starch, milk sugar, and the like. It may also be administered orally in the form of solutions or suspensions, or it may be injected parenterally. For parenteral administration it may be used in the form of sterile solution or suspension containing other solutes, for example, enough saline or glucose to make the solution isotonic.

The physician or veternarian will determine the dosage, and it will vary with the form of administration and the severity of the need for vasodilation by the patient under treatment. Generally, treatment is initiated with small dosages substantially less than the optimum dose of the compound. Thereafter, the dosage is increased by small increments until the optimum effect under the circumstances is reached. In general, the compound of this invention is most desirably administered at a concentration level that will generally afford effective results without causing any harmful or deleterious side effects and preferably at a level that is in the range of from about 100 mg to about 750 mg per kilo per day although variations will occur in special instances. Dosage unit forms containing these amounts, or other amounts may be provided.

The following non-limiting examples are given by way of illustration only.

EXAMPLE 1

To a solution containing 66.11 g (0.59 mol) of nitronium tetrafluoroborate in 250 ml of dry sulfolane (distilled over calcium hydride at a reduced pressure) is added 45 g (0.65 mol) of isoxazole during a period of two hours while maintaining the temperature at 21° C. to 26° C. After addition is completed, the yellow mixture is stirred at ambient temperature and poured onto ice. The mixture is extracted with three 300 ml portions of ether, the extracts combined and washed with five 100 ml portions of water. The ether layer is separated, dried over anhydrous sodium sulfate for two hours, filtered, and the ether removed at reduced pressure to leave an orange liquid which still contains appreciable quantities of water and evolves nitrous oxides. The crude material is adsorbed on a silica gel column (200 ml) and eluted with 1.5 liters of chloroform. Concentration of the eluent at reduced pressure affords a yellow oil which crystalizes on standing at ambient temperature (23.22 g: 35% yield).

A sample recrystallized from 3:7 ether-hexane with charcoal crystallizes as yellow plates; m.p. 46°–47.5° C.

EXAMPLE 2

Preparation Of Tablets

500 G of 4-nitroisoxazole and 1000 g of lactose are thoroughly mixed together and the whole passed through a 30 mesh sieve.

A paste is separately prepared with 40 g of corn starch and 175 ml of distilled water.

The above mixture is well kneaded with the paste, the mass passed through a 4 mesh sieve and the resulting globules were dried at 25° C. in a stream of warm air for 15 hours.

The dried globules are granulated first on a granulating machine and then passed through a 16 mesh sieve. The grains are covered with a powdery mixture prepared by blending 15 g of calcium stearate, 100 g of corn starch and 40 g of talc, and then passed through a 40 mesh sieve.

Tablets each containing 125 mg of 4-nitroisoxazole are made in accordance with the conventional procedure known in the art.

EXAMPLE 3

Preparation Of Injection

100 G of 4-nitroisoxazole is taken up in 500 ml of distilled pyrogen free water and made up to 5 liters. The solution is made isotonic by addition of a predetermined amount of an aqueous solution of physiological salt.

EXAMPLE 4

Preparation Of An Aqueous Suspension For Oral Administration

A mixture consisting of:

| | |
|---|---|
| 4-Nitroisoxazole | 20.0 g |
| Cane Sugar | 100.0 g |
| Glycerine | 100.0 ml |
| Ethyl p-hydroxybenzoate | 1.5 g |
| Artificial orange essence | 0.2 ml |
| Essential oil of orange | 1.0 ml | is added to one liter of distilled water.

What is claimed is:

1. A pharmaceutical composition containing an amount of 4-nitroisoxazole which is effective to cause vasodilation in a patient needing such treatment together with a pharmaceutically acceptable excipient.
2. A composition of claim 1 in solid form.
3. A composition of claim 1 in liquid form.
4. A pharmaceutical composition in dosage unit form, each dosage unit containing an amount of 4-nitroisoxazole which is effective to cause vasodilation in a patient needing such treatment together with a pharmaceutically acceptable excipient.
5. A composition as in claim 4 in solid form.
6. A composition as in claim 4 in liquid form.
7. A composition as in claims 4, 5 or 6 containing from 100 mg to 750 mg of 4-nitroisoxazole per dosage unit.
8. A method of treating a patient in need of vasodilation which comprises administering to such a patient a pharmaceutical composition containing an amount of 4-nitroisoxazole which is effective to cause vasodilation in a patient needing such treatment together with a pharmaceutically acceptable excipient.
9. A method as in claim 8 wherein the composition is in solid form.
10. A method as in claim 8 wherein the composition is in liquid form.

* * * * *